United States Patent
Qinwei

(10) Patent No.: US 8,119,393 B2
(45) Date of Patent: *Feb. 21, 2012

(54) MEMBRANE ARRAY AND ANALYTICAL DEVICE

(75) Inventor: Shi Qinwei, Richmond Hill (CA)

(73) Assignee: ZBX Corporation, Toronto, Ontario (CA)

(*) Notice: Subject to any disclaimer, the term of this patent is extended or adjusted under 35 U.S.C. 154(b) by 891 days.

This patent is subject to a terminal disclaimer.

(21) Appl. No.: 11/993,013

(22) PCT Filed: Jun. 28, 2006

(86) PCT No.: PCT/CA2006/001065
§ 371 (c)(1),
(2), (4) Date: Dec. 18, 2007

(87) PCT Pub. No.: WO2007/000048
PCT Pub. Date: Jan. 4, 2007

(65) Prior Publication Data
US 2010/0137145 A1    Jun. 3, 2010

Related U.S. Application Data

(60) Provisional application No. 60/694,239, filed on Jun. 28, 2005.

(51) Int. Cl.
*G01N 33/53*        (2006.01)
(52) U.S. Cl. .................. 435/287.8; 435/287.9; 435/970; 435/971; 422/429; 422/430; 436/518; 436/528
(58) Field of Classification Search .................. None
See application file for complete search history.

(56) References Cited

U.S. PATENT DOCUMENTS

| | | |
|---|---|---|
| 4,094,647 A | 6/1978 | Deutsch et al. |
| 4,235,601 A | 11/1980 | Deutsch et al. |
| 4,361,537 A | 11/1982 | Deutsch et al. |
| 4,703,017 A | 10/1987 | Campbell et al. |
| 4,774,192 A | 9/1988 | Terminiello et al. |
| 4,839,297 A | 6/1989 | Freitag et al. |
| 4,861,711 A | 8/1989 | Freisen et al. |
| 4,885,240 A | 12/1989 | Wu |
| 4,960,691 A | 10/1990 | Gordon et al. |
| 5,075,078 A | 12/1991 | Osikowicz et al. |
| 5,079,142 A | 1/1992 | Coleman et al. |
| 5,110,724 A | 5/1992 | Hewett |
| 5,120,643 A | 6/1992 | Ching et al. |
| 5,135,716 A | 8/1992 | Thakore |
| 5,290,678 A | 3/1994 | Jackowski |
| 5,354,692 A | 10/1994 | Yang et al. |
| 5,468,648 A | 11/1995 | Chandler |
| 5,559,041 A | 9/1996 | Kang et al. |
| 5,591,645 A | 1/1997 | Rosenstein |
| 5,607,863 A | 3/1997 | Chandler |

(Continued)

FOREIGN PATENT DOCUMENTS

EP    0 852 336 B1    7/1998

(Continued)

*Primary Examiner* — Bao Thuy L Nguyen
(74) *Attorney, Agent, or Firm* — Sim & McBurney

(57) ABSTRACT

A membrane array used to detect one or more analytes from a small sample of fluid with high sensitivity is provided. The membrane array can be employed in various analytical devices and is especially useful for identifying analytes from whole blood with minimal or negligible background interference.

46 Claims, 10 Drawing Sheets

U.S. PATENT DOCUMENTS

| | | | |
|---|---|---|---|
| 5,622,871 A | 4/1997 | May et al. | |
| 5,648,274 A | 7/1997 | Chandler | |
| 5,656,503 A | 8/1997 | May et al. | |
| 5,728,587 A * | 3/1998 | Kang et al. | 436/518 |
| 5,846,838 A | 12/1998 | Chandler | |
| 5,869,345 A | 2/1999 | Chandler | |
| 5,877,028 A | 3/1999 | Chandler et al. | |
| 5,998,220 A | 12/1999 | Chandler | |
| 6,017,767 A | 1/2000 | Chandler | |
| 6,168,956 B1 | 1/2001 | Chandler | |
| 6,171,870 B1 | 1/2001 | Freitag | |
| 6,187,598 B1 | 2/2001 | May et al. | |
| 6,214,629 B1 | 4/2001 | Freitag et al. | |
| 6,228,660 B1 | 5/2001 | May et al. | |
| 6,528,321 B1 | 3/2003 | Fitzgerald et al. | |
| 6,534,320 B2 | 3/2003 | Ching et al. | |

FOREIGN PATENT DOCUMENTS

| | | | |
|---|---|---|---|
| JP | H02-55952 | | 2/1990 |
| JP | H10-10125 | | 1/1998 |
| JP | 2000-146959 | | 5/2000 |
| JP | 2001-124771 | | 5/2001 |
| JP | 2005-009888 | | 1/2005 |
| JP | 2005-024325 | | 1/2005 |
| WO | WO 94/06013 | | 3/1994 |
| WO | WO 96/35952 | | 11/1996 |
| WO | WO 97/18036 | | 5/1997 |
| WO | WO 97/34148 | | 9/1997 |
| WO | WO 01/29558 | | 4/2001 |
| WO | WO 01/31337 A | | 5/2001 |
| WO | WO 03/008933 | | 1/2003 |
| WO | PCT/IB2003/005088 | | 4/2004 |
| WO | WO 2004/033101 | * | 4/2004 |
| WO | WO 2004/033101 A | | 4/2004 |

* cited by examiner

MEMBRANE ARRAY AND ANALYTICAL DEVICE

RELATED APPLICATIONS

Benefit of priority is claimed under 35 U.S.C. 119(e) to U.S. Provisional Application No. 60/694,239 filed on Jun. 28, 2005 and International Application No: PCT/CA2006/001065 filed on Jun. 28, 2006. The disclosures of the above-referenced applications are fully incorporated by reference.

FIELD OF THE INVENTION

This invention relates to analytical devices and methods useful for analytical assays of fluid samples. More specifically, the invention is directed to a novel membrane array and analytical devices incorporating same. The invention is useful for rapidly determining the presence of one or more analytes in small volumes of sample.

BACKGROUND OF THE INVENTION

Immunoassay devices and procedures currently exist for detecting the presence of an analyte in a sample of biological fluid. Typically, immunochemical reactions involving antigen/antibody reactions take place on dry porous carriers such as cellular membranes through which the sample to be analyzed flows by capillary action. The presence of an analyte in the sample can be detected either visually or by using reflectance or fluorescence based detection systems and instruments. Oftentimes, the label is an enzyme label or a particulate direct label, for instance a gold sol label.

Typical immunochromatographic devices of this nature are described in the following U.S. Pat. Nos. 4,094,647; 4,235,601; 4,361,537; 4,703,017, 4,774,192; 4,839,297; 4,861,711; 4,885,240; 4,960,691; 5,075,078; 5,079,142; 5,110,724; 5,120,643; 5,135,716; 5,468,648; 5,591,645; 5,607,863; 5,622,871; 5,648,274; 5,656,503; 5,846,838; 5,869,345; 5,877,028; 5,998,220; 6,017,767; 6,168,956; 6,171,870; 6,187,598; 6,214,629B1; 6,228,660; 6,528,321; and 6,534,320.

U.S. Pat. No. 5,290,678 describes an analytical test kit incorporating a dry chemistry membrane comprising antibody pairs to multiple analytes observed during cardiovascular events. In operation of the device, multiple transfer steps are required before analysis and further this device is only designed for receiving samples of serum or plasma and as such is not suitable for analyses using whole blood.

U.S. Pat. No. 5,559,041 discloses an immunoassay device with a membrane array comprising an overlapping arrangement of a reservoir pad, numerous membrane filters and a wicking membrane all with an equal range of pore sizes. In the use of this device, rapid and high sensitivity analysis of analyte concentrations cannot be achieved with small sample sizes.

PCT/IB2003/005088 describes a membrane array and analytical device designed for the sensitive detection of analytes from a sample of fluid as small as a drop. The membrane array comprises a two membrane system including a first separation membrane and an analytical capture membrane. However, rapid and high sensitivity detection of analytes using whole blood is not achievable in all circumstances and membrane array constructions with small sample volumes without background interference caused by hemolysis (the liberation of hemoglobin from the red blood cell).

While the aforementioned devices are generally useful for detecting analytes in a sample, it is desirable to provide an analytical device which has greater sensitivity using smaller sample volumes and at the same time provides a rapid test result. Thus, there is a need to develop an analytical device that is designed to obviate some of the deficiencies of the prior art devices.

SUMMARY OF THE INVENTION

The present invention is an improved membrane array and analytical device that is used to rapidly detect one or more analytes from small volume samples in one step with high efficiency and high sensitivity compared to any type of membrane arrays of the prior art. In aspects, the invention is especially suitable for use with small samples of whole blood with minimal hemolysis.

According to an aspect of the present invention is an improved membrane array that accommodates small sample volumes and provides rapid, highly efficient and highly sensitive detection of one or more analytes in the small sample volume.

According to another aspect of the present invention is an improved membrane array that accommodates small whole blood sample volumes and is capable of rapid, highly efficient and highly sensitive detection of one or more analytes in the whole blood sample volumes with substantially minimal or negligible hemolysis of the whole blood.

According to another aspect of the present invention is an improved membrane array that accommodates small sample volumes and is capable of rapid, highly efficient and highly sensitive detection of one or more analytes in the sample, the membrane array comprising three or more porous membranes, each of which is arranged in a manner to be in non-planar contact with respect to adjacent ones.

According to another aspect of the present invention is an improved membrane array that accommodates small whole blood sample volumes and is capable of rapid, highly efficient and highly sensitive detection of one or more analytes in the whole blood sample volumes with minimal or negligible hemolysis of the whole blood, the membrane array comprising three or more porous membranes, each of which is arranged in a manner to be in non-planar contact with respect to adjacent ones.

According to another aspect of the present invention there is provided a membrane array, said membrane array comprising:
at least three overlapping porous membranes arranged in stair step configuration comprising;
a first step adapted to receive a fluid sample and containing a detection reagent;
a second step having a lower porosity than said first step; and
a third step having a lower porosity than said second step and containing a capture reagent.

According to yet another aspect of the present invention there is provided a membrane array, said membrane array comprising:
at least three overlapping porous membranes arranged in stair step configuration comprising;
a first step adapted to receive a small sample of whole blood, said first step being retardant of red blood cells and containing a detection reagent;
a second step having a porosity that is further retardant of red blood cells compared to said first step with minimal hemolysis of the sample; and
a third step having a lower porosity than said second step and containing a capture reagent.

According to another aspect of the present invention is an analytical device comprising a membrane array of the present invention.

According to still another aspect of the present invention is an analytical device for the detection of an analyte in a small volume of sample, the device comprising:
- a membrane array having at least three overlapping porous membranes arranged in stair step configuration, the membrane array comprising;
- a first step adapted to receive a fluid sample and containing a detection reagent;
- a second step having a lower porosity than said first step; and
- a third step having a lower porosity than said second step and containing a capture reagent.

According to yet another aspect of the present invention is an analytical device useful for the rapid and highly sensitive detection of at least one analyte in a drop of sample; the analytical device comprising:
- a membrane array of at least three overlapping porous membranes arranged in stair step configuration the membrane array comprising; a first step adapted to receive a fluid sample and containing a detection reagent; a second step having a lower porosity than said first step; and a third step having a lower porosity than said second step and containing a capture reagent;
- the membrane array being enclosed in a platform formed with sample application means and a sample flow channel, where said sample flow channel directs flow of sample from sample application means to the first step wherein the sample flows substantially horizontally into the first step through a thickness of the membrane edge and wherein the sample flows by capillarity through the second step to the third or subsequent steps of said membrane array.

According to yet another aspect of the present invention is an analytical device comprising;
- a membrane array supported within an analytical device housing having a first and a second end, wherein one end is adapted to receive a removable cap, said cap facilitating the application of a sample to said membrane array via a sample flow channel.

In aspects, the membrane array can be a two membrane or a three or more membrane stair step configuration as described herein. In further aspects, the application of a sample may be done via a pipette for example.

In yet another aspect of the present invention there is provided an analytical device, the device comprising;
- a membrane array supported within an analytical device housing having a first and a second end, wherein one end is adapted to be immersed in a sample such that sample is provided to said membrane array.

In aspects, the membrane array can be a two membrane or a three or more membrane stair step configuration as described herein.

According to another aspect of the present invention is a method for determining the amount of analyte in a small volume fluid sample, said method comprising;
providing a membrane array comprising;
- a first step adapted to receive a fluid sample and containing a detection reagent;
- a second step having a lower porosity than said first step; and
- a third step having a lower porosity than said second step and containing a capture reagent; and
applying a fluid sample to one end of said first step via a sample flow channel, wherein said fluid sample moves into the first step horizontally through the thickness of a membrane edge via capillary flow and moves to said second step and then to said third step where capture of said analyte occurs.

In aspects, the membrane array has more than three steps and the fluid sample moves from first, to second, to third and subsequent steps as herein described.

In aspects of the invention, the fluid sample is a small volume of whole blood.

According to yet another aspect of the present invention is a one step method for detecting an analyte in a fluid sample, the method comprising;
applying a fluid sample to a membrane array comprising;
- a first step adapted to receive a fluid sample and containing a detection reagent; a second step having a lower porosity than said first step; and a third step having a lower porosity than said second step and containing a capture reagent;
wherein said fluid sample is applied via a sample flow channel, horizontally through a thickness of the membrane edge, to one end, of said first step, said fluid sample moving via capillary flow to said second step and then to said third step where detection of said analyte occurs.

According to another aspect of the present invention there is provided an improved membrane array that accommodates small sample volumes and provides rapid, highly efficient and highly sensitive detection of one or more analytes in the sample, the membrane array comprising three or more porous membranes which are non-planar with respect to adjacent ones.

According to another aspect of the present invention there is provided an improved membrane array that accommodates small sample volumes and provides rapid, highly efficient and highly sensitive detection of one or more analytes in the sample, the membrane array comprising three or more porous membranes each of which has a different porosity, said porous membrane being non-planar with respect to adjacent ones.

According to another, aspect of the present invention there is provided an analytical device for the rapid detection of a component in a small volume of sample, the analytical device comprising:
- a membrane array having at least three overlapping porous membranes arranged in stair step configuration comprising;
- a first step adapted to receive a fluid sample and containing a detection reagent;
- a second step having a lower porosity than said first step; and
- a third step having a lower porosity than said second step and containing a capture reagent.

According to another aspect of the present invention there is provided an analytical device useful for the rapid and highly sensitive detection of at least one analyte in a drop of sample; the analytical device comprising:
- a membrane array of at least three overlapping porous membranes arranged in stair step configuration the membrane array comprising; a first step adapted to receive a fluid sample and containing a detection reagent; a second step having a lower porosity than said first step; and a third step having a lower porosity than said second step and containing a capture reagent;
- the membrane array being enclosed in a platform formed with a sample application means and a sample flow channel, where said sample flow channel directs flow of sample from the sample application means to the first step where the sample flows by capillarity into and through the second step to the third step of said membrane array.

According to another aspect of the present invention there is provided an analytical device comprising;
a membrane array supported within an analytical device housing having a first and a second end, wherein one end is adapted to receive a removable cap, said cap facilitating the application of a sample using a sample transfer means to said membrane array.

According to another aspect of the present invention there is provided an analytical device, the device comprising;
a membrane array supported within an analytical device housing having a first and a second end, wherein one end is adapted to be immersed in a sample such that the sample is provided to said membrane array through the immersed end of said analytical device.

According to another aspect of the present invention there is provided a method for determining the amount of analyte in a small volume fluid sample, said method comprising;
providing a membrane array comprising;
a first step adapted to receive a fluid sample and containing a detection reagent;
a second step having a lower porosity than said first step; and
a third step having a lower porosity than said second step and containing a capture reagent; and
applying a fluid sample to one end of said first step, wherein said fluid sample moves via capillary flow into and through said second step and then to said third step where detection of said analyte occurs.

According to another aspect of the present invention there is provided an improved membrane array that accommodates small sample volumes and is capable of rapid, highly efficient and highly sensitive detection of analytes in the sample, the membrane array comprising at least three porous membranes which are non-planar with respect to adjacent membranes.

According to another aspect of the present invention there is provided an analytical device for the rapid detection of a component in a small volume of sample, the analytical device comprising:
a membrane array having at least three overlapping porous membranes arranged in stair step configuration comprising;
a first separation membrane adapted to receive a fluid sample and containing a detection reagent;
a second separation membrane downstream from said first separation membrane and having a lower porosity than said first separation membrane; and
an analytical membrane downstream from said second separation membrane having a lower porosity than said second separation membrane and containing a capture reagent.

According to another aspect of the present invention there is provided an analytical device useful for the rapid and highly sensitive detection of at least one analyte in a drop of sample; the analytical device comprising:
a membrane array of at least three overlapping porous membranes arranged in stair step configuration, the membrane array comprising;
a first separation membrane adapted to receive a fluid sample and containing a detection reagent;
a second separation membrane downstream from said first separation membrane and having a lower porosity than said first separation membrane; and
an analytical membrane downstream from said second separation membrane and having a lower porosity than said second separation membrane and containing a capture reagent.

the membrane array being housed in a platform formed with a sample application means and a sample flow channel, wherein said sample flow channel directs flow of sample from the sample application means to the first separation membrane where the sample flows into through the second separation membrane to the analytical membrane of said membrane array.

According to another aspect of the present invention there is provided an analytical device for the rapid detection of an analyte in a small volume of sample, the analytical device comprising:
a membrane array having at least three overlapping porous membranes arranged in stair step configuration;
a sample application means for receiving said sample;
a sample flow channel in fluid communication with said sample application means, said sample flow channel dimensioned to provide for substantially uniform horizontal flow of said sample into said membrane array.

According to another aspect of the present invention there is provided an a method for detecting an analyte in a fluid sample, the method comprising;
applying a fluid sample to a membrane array comprising;
a first separation membrane adapted to receive a fluid sample and containing a detection reagent; a second separation membrane downstream of said first separation membrane and having a lower porosity than said first separation membrane; and a analytical membrane downstream from said second separation membrane having a lower porosity than said second separation membrane and containing a capture reagent;
wherein said fluid sample is applied via a sample flow channel to one end of said first separation membrane, said fluid sample moving via capillary flow to said second separation membrane and then to said analytical membrane where detection of said analyte occurs.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments will now be described, by way of example only, with reference to the attached figures, wherein.

DETAILED DESCRIPTION OF THE INVENTION

Glossary

Figure 1:
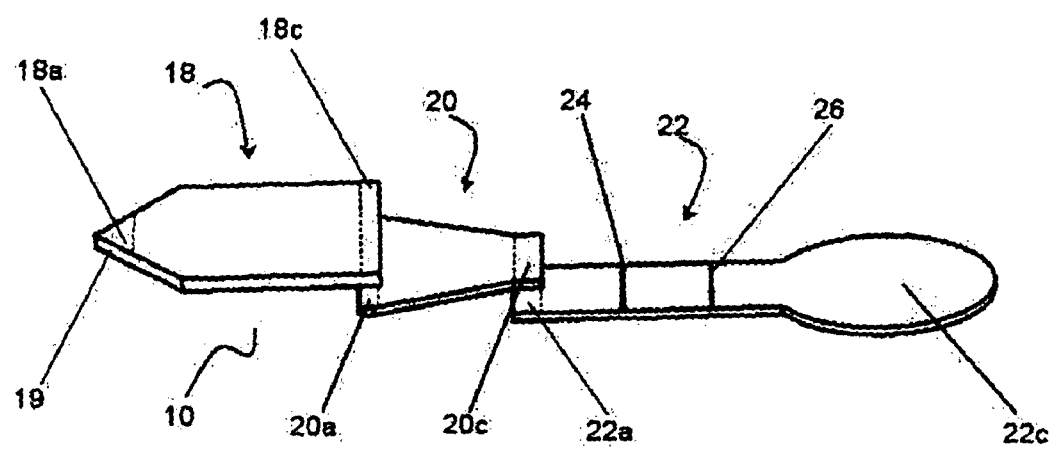
FIG. 1 is a perspective view of the membrane array of the invention.

The following terms have the following general meaning as they are employed in the description of the invention and in the claims.

"Analytical device" is a combination of a membrane array and a support platform comprising upper and lower halves which are brought into registry to hold and support the membrane array. These halves are generally prepared from a rigid plastic such as but not limited to polyacrylate or polymethacrylate. They may be formed into the desired configuration for cooperation with the dry porous carriers to form channels by molding, stamping, machining or any equivalent type process. The channels may be formed in the dry porous layers by stamping from a strip of the selected porous material or with a hydrophobic substance such as wax or ink.

"Antigen" is a molecule which, in a mammal, induces the production of an antibody. The devices of this invention are useful for determining the presence of antigens or antibodies in whole blood or any other type of body fluids. Antigens are often referred to as "analytes" because they are characteristic of specific physiological conditions such as infections, cancer or pregnancy.

"Capture reagent" is a material, often a second antibody to the analyte which is to be detected in the liquid sample. It is fixed to the carrier downstream of the detecting reagent. It reacts with and concentrates the complex on the carrier to form a product which is visible to the naked eye or readable with the aid of a suitable instrument.

"Cardiac analytes" are analytes which are released into the blood as a result of cardiac tissue deterioration.

"Channel" is any formed conduit in the analytical device through which the fluid sample under analysis flows. Channels are said to be in operative communication when a fluid in one channel flows substantially directly into another.

"Control reagent" is any reagent that reacts with either the detection reagent or another component separate from an analyte in a sample to provide a visible product and thereby advise the operator that the sample has reached analytical membrane.

"Detection reagent" is a material, often an antibody to the analyte which is to be detected in the liquid sample. It is typically releasably bound to the dry porous carrier at or downstream of the application point for the liquid sample. For most immunochemical analyses, it is labeled with a detectable label such as colloidal gold and forms a complex with the analyte to be determined.

"Efficient" means that a detectable product can be formed with a low/small volume of fluid, e.g. just one drop of whole blood (about 10 µl to about 50 µl), utilizing small amounts of reagents even when the antigen is present in very low/small concentrations as is usually the case with most analytes such as for example with the cardiac analyte troponin I (cTnI).

"Membrane array" refers to a cellular product through which the sample to be analyzed moves by capillary action. As will be seen by the figures and understood by description of the invention, an array of three or possibly more membrane segments are arranged in stair step configuration for capillary flow.

"Rapid" means that a detectable product forms within a sufficiently short period of time relative to detection times of current technologies measuring the same analyte, e.g. within about 2 to about 30 minutes, to permit the medical attendant to draw meaningful and useful conclusions. Furthermore, it can be appreciated that the time required for the analysis will vary depending on the particular analytes in question.

The present invention is a novel membrane array and analytical devices incorporating such, the membrane array and analytical devices permitting rapid, highly efficient and highly sensitive detection of a desired analyte(s). In aspects, the detection may be qualitative, semi-quantitative or substantially quantitative. This membrane array comprises at least three membrane layers arranged in a stair-step configuration where the pore size decreases in each successive step. This membrane array is particularly suited for the rapid analysis of analytes and components of fluid samples and in particular the analysis of small volumes of fluid samples. In aspects, the invention is particularly suited for the rapid analysis of components of whole blood using a one step procedure. The analysis is conducted with minimal invasiveness as only a small amount of blood is required to obtain high sensitivity detection without background interference and with minimal hemolysis. Small volumes of whole blood can readily be provided with a any type of finger lancet or pin prick to the finger for example. Furthermore, the membrane array of the invention can be adapted for use in a variety of analytical device configurations. The membrane array and analytical device incorporating such are easy to manufacture, do not require separate sample collection or transfer devices for capillary blood samples and may require a separate timing device. Furthermore, the test result is relatively stable for a long time period. Rapid and accurate diagnoses using small volumes of sample is provided by the present invention.

The invention is now herein described with reference to FIG. 1 which shows a membrane array designated generally as reference numeral 10. The membrane array 10 comprises three overlapping porous membranes arranged in a stair-step configuration, that is, the layers are non-planar with respect to adjacent ones. The first step is a first separation membrane 18, the second step is a second separation membrane 20 and the third step is an analytical membrane 22. The first separation membrane has an upstream end 18a, a downstream end 18c and first separation membrane edge 19. The first separation membrane 18 performs the initial filtration of the sample, and in the case of a drop of whole blood, the first separation membrane 18 acts to hinder the downstream movement of the whole red blood cells. The first separation membrane 18 also contains at least one detection reagent for the analyte of interest such as for example a labeled antibody to an epitope on the analyte to form a labeled antigen/antibody complex. The second separation membrane 20 is selected to have a smaller pore size than the first separation membrane 18 and a larger pore size than the analytical membrane 22. The second separation membrane 20 has an upstream end 20a and a downstream end 20c. When the sample applied is a drop of whole blood, the second separation membrane 20 serves to further retard the downstream movement of whole red blood cells in the sample with minimal hemolysis. The analytical membrane 22 contains the capture reagent and has an upstream end 22a and a downstream end 22c.

The first separation membrane 18 is formed from any type of porous membrane material that is blood compatible and in general, body fluid compatible. Such material may be selected for example but not limited to nitrocellulose, PVDF (polyvinylidene difluoride), glass fiber such as Whatman F87-14, synthetic fiber membranes available from Pall Corporation (Long Island, N.Y.) and polyethersulfone and pyrrolidone membranes available from Spectral Diagnostics (Toronto, Canada). One of skill in the art would understand that any similar type of such materials as disclosed herein would be suitable for use in the invention. The pore size of the first separation membrane 18 is selected so that it is greater than the pore size of the second separation membrane 20. In aspects of the invention the pore size of the first separation membrane 18 may be selected from a pore size of about 8 µm to about 60 µm (and any range there-in-between). Such ranges may include but not be limited to from about 8 µm to about 10 µm, from about 8 µm to about 20 µm, from about 8 µm to about 30 µm, from about 8 µm to about 40 µm and from about 8 µm to about 50 µm. This also includes sub-ranges of these ranges.

The second separation membrane 20 is similarly formed from any type of porous membrane material that is blood compatible and in general body fluid compatible as would be understood by one of skill in the art. In aspects, the second separation membrane is formed from nitrocellulose selected with a pore size that is smaller than the pore size of the first separation membrane 18. In preferred aspects of the invention, the pore size is selected to accommodate red blood cells without substantial hemolysis. In an aspect of this invention this pore size is about greater than the size of a red blood cell up to about 8 µm or so. The second separation membrane 20, by virtue of being of a smaller pore size than the first separation membrane 18 is a further retardant to the movement of red blood cells.

The analytical membrane 22 is formed from any porous membrane material that binds protein with high affinity as is understood by one of skill in the art such as but not limited to nitrocellulose and PVDF (polyvinylidene difluoride). In aspects of the invention nitrocellulose is used and is selected to have a pore size that is less than that of the second separation membrane 20. In an aspect of the invention this membrane has a smaller porosity than the second separation membrane 20. Because of its small pore size, the analytical membrane 22 can bind a large amount of capture reagent, for example, an antibody which reacts with a second epitope on the analyte forming a detectable labeled antibody-analyte/antigen product at the capture line 24. The capture reagent may also be an antigen. The increased amount of capture reagent results in high sensitivity of the analytical devices of the invention. Analytical membrane 22 may optionally contain a control line 26 that may contain a control reagent which reacts with either the detection reagent or another component separate from the analyte in the sample to provide a visible product and thereby advise the operator that the sample has passed through the second separation membrane 20 and reached analytical membrane 22.

In embodiments of the invention, the membrane array 10 may be optionally provided with a backing strip otherwise known as a backing card for support (not shown). Typically the backing card is a polystyrene tape with an appropriate adhesive that will not migrate in the membrane array 10. One such polystyrene tape is Super White® polystyrene tape (G & L Precision Die Cutting, Inc, San Jose, Calif.). A transparent cover tape may also be utilized over each or all of the membranes 18, 20 and 22 to inhibit evaporation of the sample. A typical transparent cover tape suitable for use with the invention is ARcare® which is a polyester film about 50 µm thick (Adhesives Research, Glenn Rock, Pa.).

The membrane array of the present invention may be fabricated in a variety of sizes and shapes and is not limited to that specifically shown in FIG. 1 as is understood by one of skill in the art. The fabrication of the membrane array may be accomplished to be accommodated in a variety of analytical devices as desired. Furthermore, while the membrane array is shown to comprise three steps, it is understood by one of skill in the art that each step may be provided as more than one membrane so long as the function of that step and thus the function of the entire membrane array, remains the same. Furthermore, the membrane array as provided with more than three steps should maintain a decreasing porosity size from the first step at one end of the membrane array to the last step of the membrane array.

Figure 2:
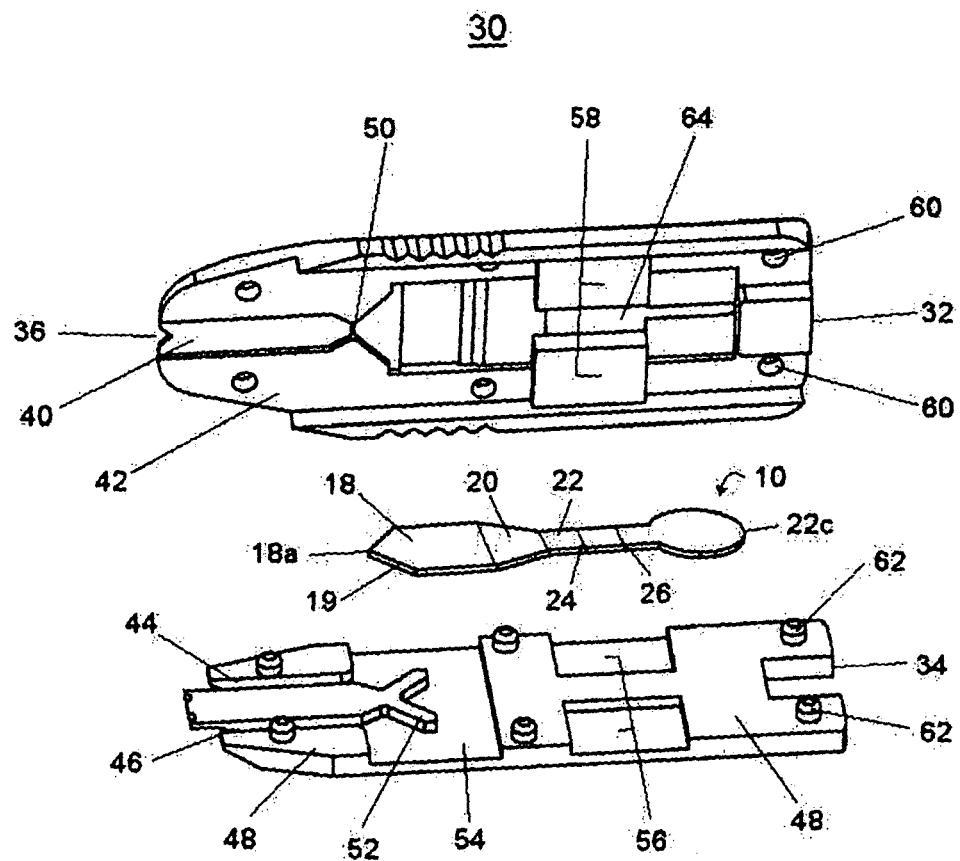
FIG. 2 is an exploded view of an analytical device incorporating the membrane array of the invention.

In one embodiment of the present invention shown in FIG. 2, is an analytical device 30 for use with the membrane array of the present invention. The device has an upper half 32 and a lower half 34 that cooperate to enclose the membrane array 10. Fluid sample entry into the analytical device 30 is from sample application means in registry with a sample flow channel formed from an indent 40 in the bottom surface 42 of upper half 32 of the device to include indent 36 in the upper half 32 of the device. There are open areas 44 and 46 where the bottom surface 42 of upper half 32 comes into contact with the top surface 48 of the lower half 34 of the device. Open areas 44 and 46 act to inhibit the flow of sample from the sample flow channel into the space between the two halves of the device. The open areas 44 and 46 extend to area 54 to prevent sample from flowing out of the membrane array 10 into the space between the two surfaces 42 and 48.

The sample flow channel terminates at the apex of the upstream end 18a of first separation membrane 18 which is supported by a Y-shaped protrusion 52 extending from the top surface 48 of lower half 34. It will be noted that the downstream end of the sample flow channel has a constriction 50 so that the sample flows horizontally and uniformly into the first separation membrane 18 at the apex 18a through the thickness of the first separation edge 19. There is also surface-to-surface contact between the first separation membrane edge 19 and the sidewalls of the widening area downstream of constriction otherwise known as the crosswise channel 50 of upper half 32. It will be noted that the first separation membrane 18 is shaped and placed so that the sample enters first separation membrane 18 at the upstream end 18a, through the thickness of the first separation edge 19 by capillary flow. From the above passages, it will be readily apparent to one skilled in the art that the greater capillary forces of the membrane array 10 than that of the sample flow channel of the analytical device 30 ensures that the analytical test only begins when a sufficient volume of sample is received.

To assist in holding the halves of the device 30 together, the top surface 48 of lower half 34 of the device contains rectangular indents 56 and cylindrical pillars 62 that are in register with rectangular protrusions 58 and cylindrical indents 60 respectively, in the bottom surface 42 of upper half 32 of the device. Features 56 and 58 also serve the additional function of holding the membrane array 10 in place.

It is shown in FIGS. 1 and 2 that the upstream end 18a of first separation membrane 18 contacts the downstream end of the crosswise channel 50 of the analytical device. Similarly the downstream end 18c of the first separation membrane 18 slightly overlaps the upstream end 20a of a second separation membrane 20. The downstream end 20c of the second separation membrane 20 in turn slightly overlaps the upstream end 22a of the analytical membrane 22. The overlapping membranes configured in a stair-step manner permit continuous flow of the sample from the sample flow channel to the crosswise channel 50 and through the membrane array 10 to its closed end 22c. To obtain rapid movement of the sample through the membrane segments and yet retain the capture line 24 and control line 26 sufficiently distanced from each other so as to be visible through the viewing window 64, the analytical membrane 22 is shaped with a narrow upstream end 22a and a circular downstream end 22c. The completion of the analytical test is indicated by the sample flow to the downstream end 22c of the analytical membrane 22 and is visibly evident through viewing window 64 in upper half 32, thus a timing device is not needed to determine test completion. Accordingly, when the fluid sample has completed its capillary flow to the downstream end 22c, the sample flow channel is substantially empty. This arrangement serves as a control to determine and to limit the volume of the sample used in the test. In this preferred embodiment, the total dimensions of the first separation membrane 18, second separation 20 and analytical membrane 22 are determined by the total absorption volume occupied by a single drop of blood which is about 10 µl to about 50 µl.

In use, a single drop of whole blood sample of sufficient quantity (about 10 µl to about 50 µl) is readily obtained with a finger lancet procedure. The blood sample is brought into contact with the membrane array 10 at the upstream end 18a of the first separation membrane 18 via the sample flow channel formed when the upper and lower halves of the analytical device 30 are assembled. The sample flows horizontally through the thickness of the first separation membrane edge 19 by capillary action into and through the first separation membrane 18 where the red blood cells are initially retarded within the first separation membrane 18. The sample then flows by capillary action towards the second separation membrane 20 where the red blood cells in the sample are further retarded and the plasma continues to flow to the downstream analytical membrane 22.

As is readily apparent, upon contact with the first separation membrane 18, the red blood cells of the sample will begin to separate from plasma and in the course of its flow the analyte will encounter a detection reagent, typically but not limited to a labeled antibody directed to an epitope of the analyte to form an analyte-detection reagent complex. The analyte-detection reagent complex then moves to the second separation membrane 20, where red blood cell migration will be further hindered/retarded. The analyte-detection reagent complex then moves toward the analytical membrane 22 and encounters a fixed capture reagent, typically but not limited to an antibody directed to a separate epitope of the analyte. The reaction of the analyte-detection reagent complex with the fixed capture reagent forms a concentrated capture line 24 visible to the naked eye or appropriate instrumentation. The optional control line 26 downstream of the capture line 24 will contain the control reagent. In aspects of the invention, the control reagent may be an anti-animal IgG. Alternatively, in place of a control line 26, variations in the length of the transparent cover tape over the membranes 18, 20 and 22 of the membrane array 10 can cause the sample when it reaches the end 22c of the analytical membrane 22 to evaporate in a controlled manner revealing a readily detectable signal.

Figure 3:
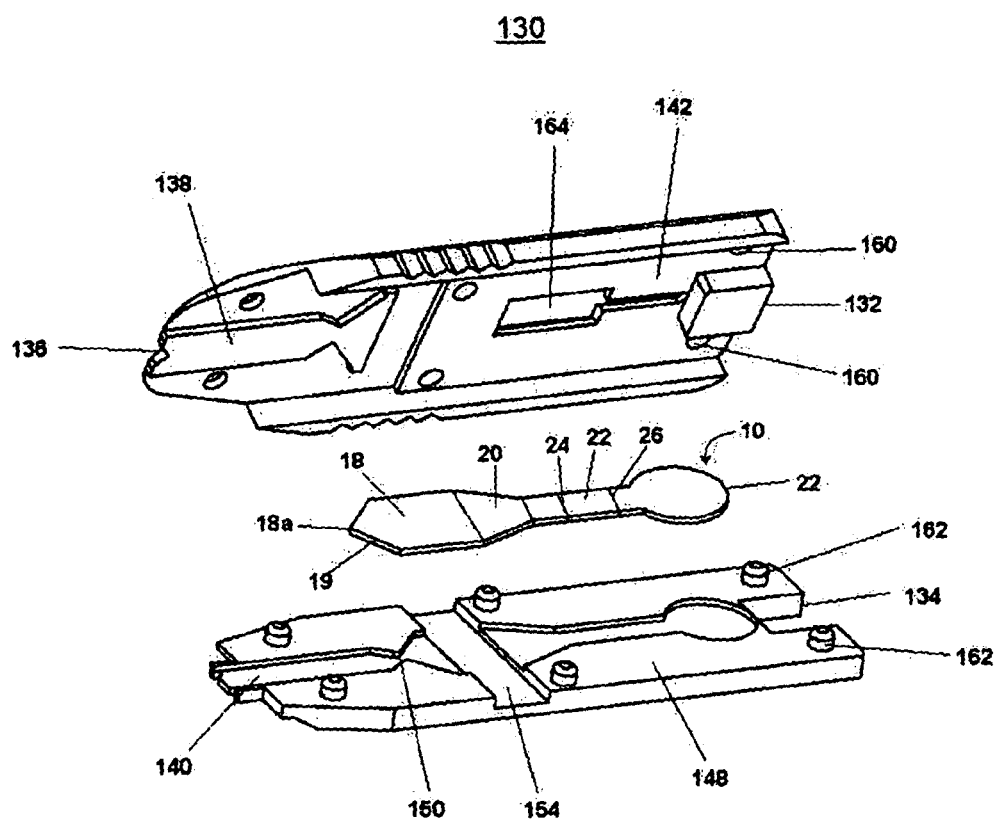
FIG. 3 is an exploded view of another embodiment incorporating the membrane array of the invention in an analytical device in which the flow channel is formed with an indent in the top surface of the lower half that incorporates the membrane array of the invention.

Another embodiment incorporating the membrane array of the present invention is shown in FIG. 3. This analytical device generally described as 130 is similar to the analytical device 30 shown in FIG. 2, except the sample flow channel is formed from a protrusion 138 in a bottom surface 142 of an upper half 132 that registers with an indent 140 in a top surface 142 of a lower half 134. Downstream from the sample flow channel is a crosswise channel 150 that widens into an open area 154. Alternatively, the sample flow channel can also be formed by a registry of indents in the bottom surface of the upper half with protrusions in the top surface of the lower half. This variation will be readily obvious to the skilled artisan and is not shown. To assist in holding the halves of the device 130 together, the top surface 142 of lower half 134 of the device 130 contains cylindrical pillars 162 that are in register with cylindrical indents 160, in the bottom surface 142 of the top half 132 of the device 130. As can be readily seen in FIG. 3, the top surface 148 of lower half 134 is provided with indents formed in the shape of the membrane array 10 which function to hold the array 10 in place in the device 130.

Figure 4:
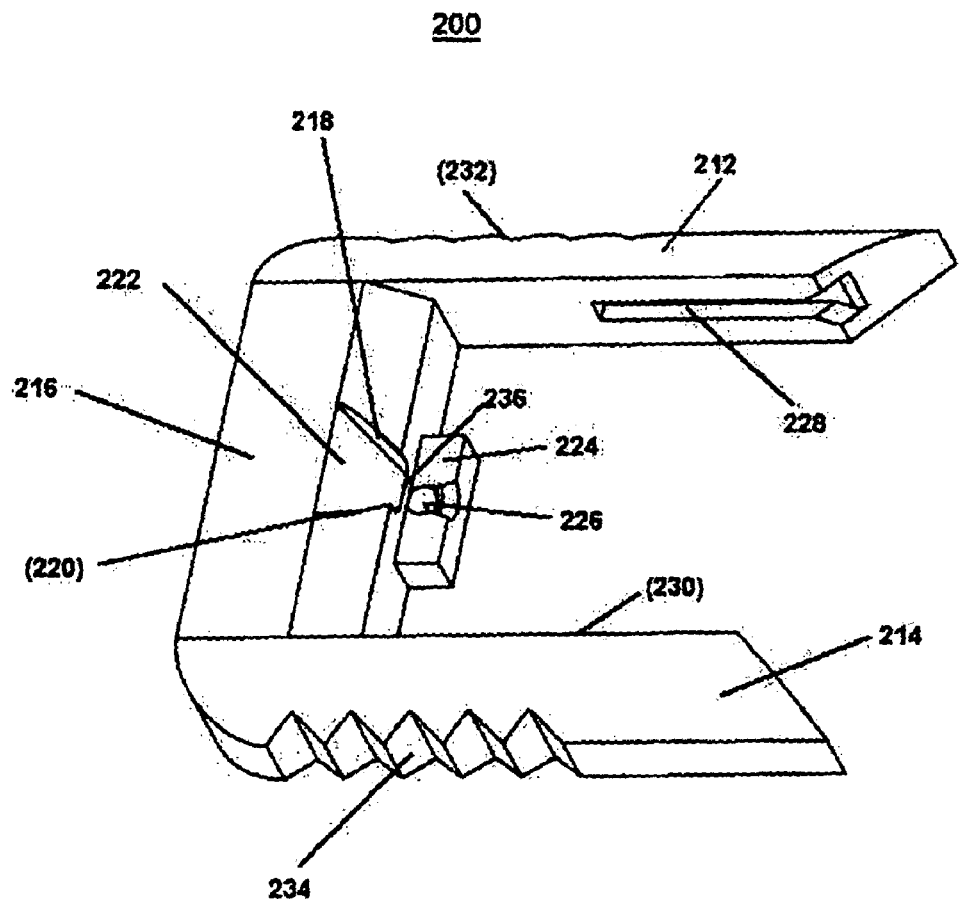
FIG. 4 is a top perspective view of a cap designed to facilitate application of a fluid sample to the analytical device and to protect the user from any contamination from the fluid sample.
Figure 5:
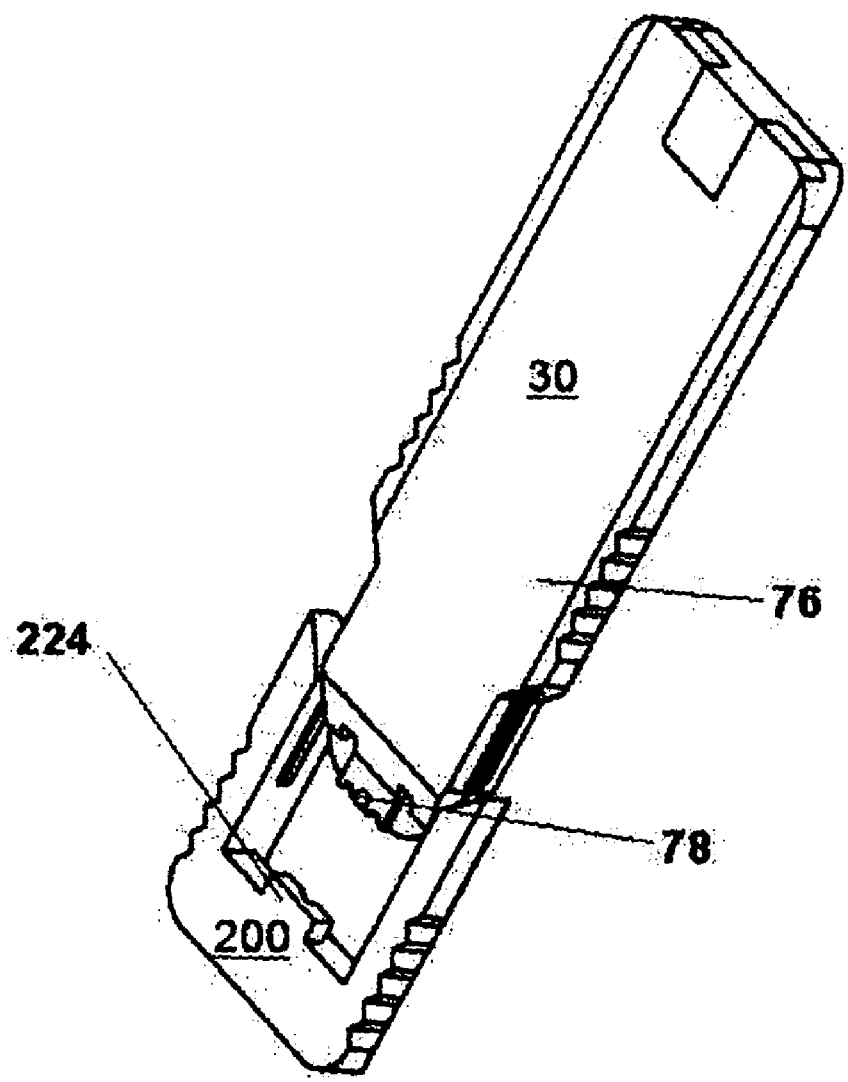
FIG. 5 is a bottom perspective view of the cap of FIG. 4 and the analytical device of FIG. 2 or 3.

Another embodiment incorporating the membrane of the present invention is a removable cap designated generally as reference numeral 200 is shown in FIG. 4 and is designed to facilitate the application of a small volume of sample using a micropipette to the analytical device and to protect the user from contamination with a fluid sample. In an embodiment, the cap is provided and fitted to serve as a guide for the placement of a sample transfer device such as micropipette tip prior to ejection of a small volume of fluid towards the sample application means of the analytical device 30. The cap 200 is formed by two guide arms 212 and 214 connected by a central body 216. Within one side of the central body 216 is an opening with side surfaces 218 and 220 and a sloping surface 222 that form a channel 236 designed to facilitate flow of fluid ejected from a pipette to the sample application means of analytical device 30. From central body 216 is a protrusion 224 with an indentation 226 that is in registry with a corresponding member 78 on the lower surface 76 of bottom half 34 at one end of analytical device 30 as shown in FIG. 5. The indentation 226 and protrusion 78 provide a snap or latch fit engagement and generally cooperate to prevent the unintentional separation of cap 200 with device 30 when fully attached as is evident from FIGS. 6 and 7.

Figure 6:
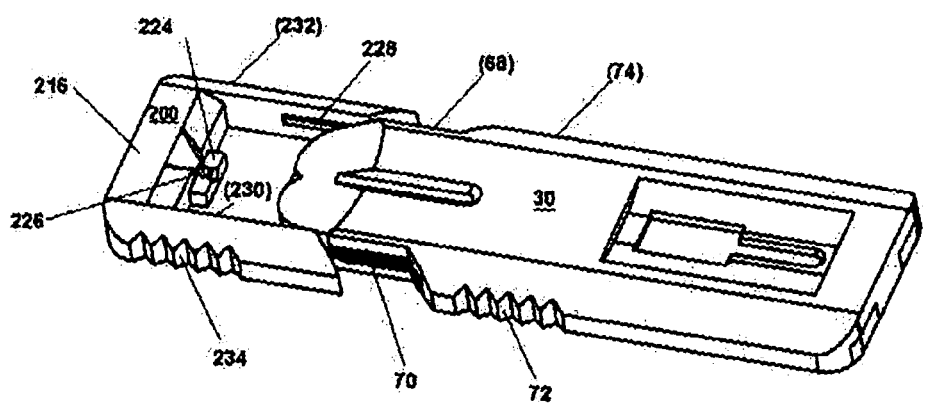
FIG. 6 is a top perspective view showing the cap of FIG. 4 for reversible engagement with the analytical device.
Figure 7:
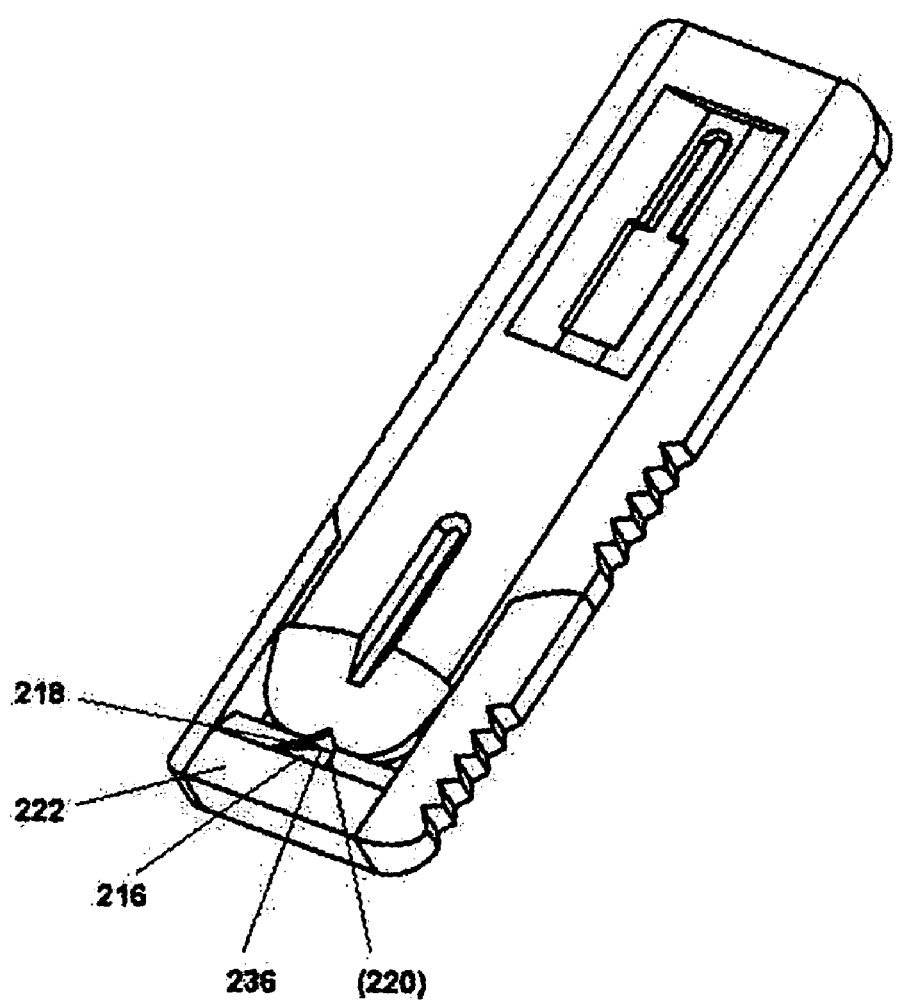
FIG. 7 is a top perspective view of showing the cap of FIG. 4 fitted on the analytical device.

FIG. 6 shows a perspective view of the cap 200 in register with an analytical device 30. The cap 200 has slots 228 and 230 that engage with corresponding guide protrusions 68 and 70, respectively, on the analytical device 30. The cap 200 can be readily engaged to the analytical device 30 by an operator's hands by using holding surfaces 232 and 234 of cap 200 to form a combination analytical device generally described as 300 which is shown in FIG. 7. As shown in FIG. 7, the central body 216 of cap 200 is abutted against analytical device 30 whereby the channel 236 of cap 200 is in operative communication with the sample application means of the analytical device 30. In use, when a fluid sample is applied via a micropipette tip, the sample flows continuously through the channel 236 to the sample application means and through the sample flow channel of the analytical device 30 to reach the membrane array 10. It is also understood and will be appreciated by those skilled in the art that the cap 200 may also be fitted to the analytical device 130 or any similar analytical device. Furthermore, it will appreciated by those skilled in the art that since the cap 200 is releasably bound to the device 30, the cap 200 may reattached after performing the finger lancet procedure to further protect the user from contamination with a fluid sample.

Figure 8:
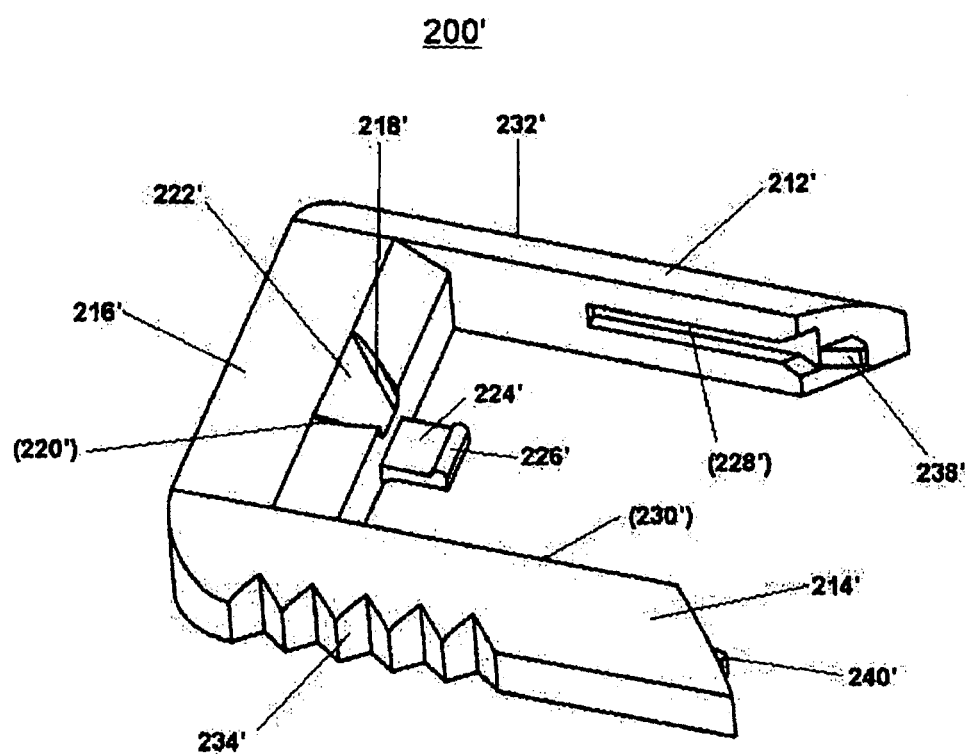
FIG. 8 is a top perspective view of another embodiment of the cap designed to facilitate application of a fluid sample to the analytical device and to protect the user from any contamination from the fluid sample.
Figure 9:
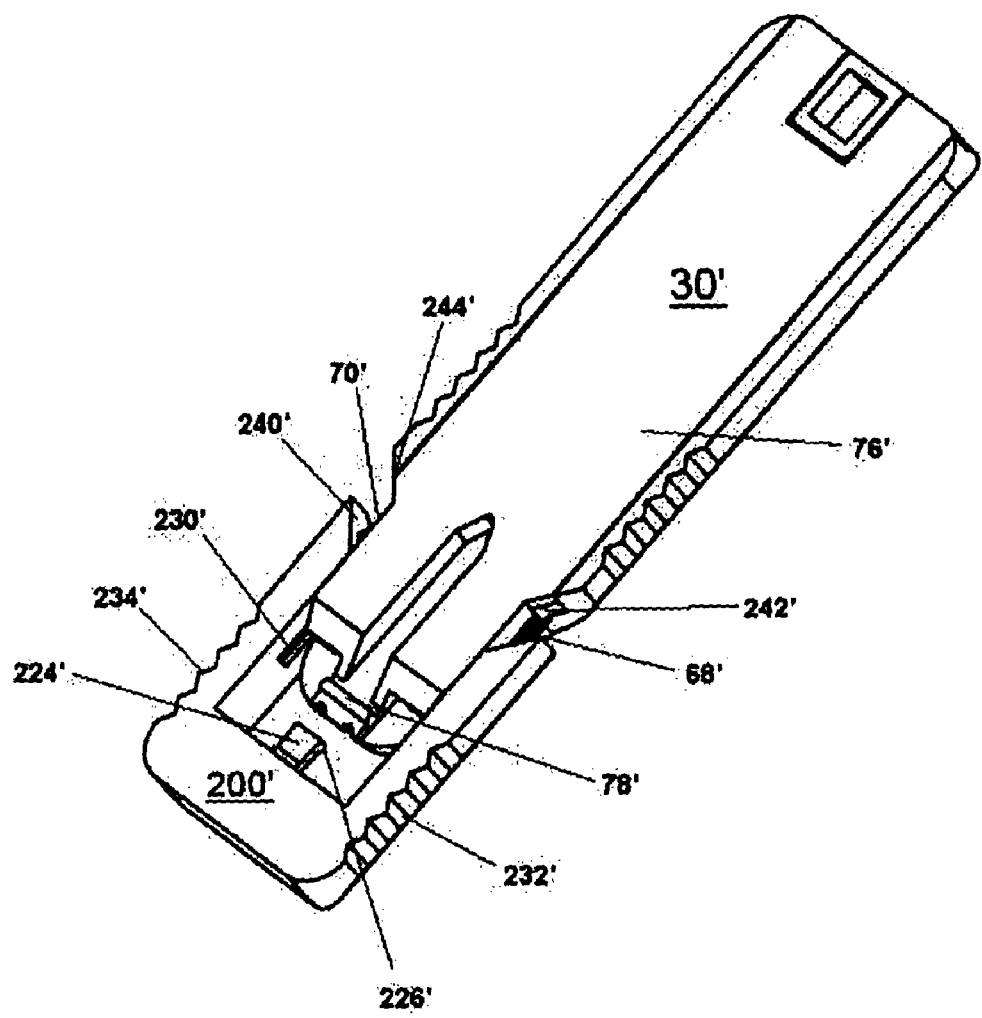
FIG. 9 is a bottom perspective view of the cap of FIG. 8 and another embodiment of the analytical device of invention.

FIG. 8 shows a perspective view of another embodiment of the removable cap designated generally as reference numeral 200'. In this embodiment, the cap 200', similar to cap 200 in that cap 200' also serves as a guide for the placement of a micropipette tip prior to ejection of a small volume of fluid towards the sample application means of an analytical device 30'. The cap 200' is formed by two guide arms 212' and 214' connected by a central body 216'. Within one side of the central body 216' is an opening with side surfaces 218' and 220' and a sloping surface 222' that forms a channel 236' designed to facilitate flow of fluid ejected from a micropipette to the sample application means of the analytical device 30'. From central body 216' is a protrusion 224' having a member 226' that is adapted to be in registry with a corresponding indentation 78' on the lower surface 76' of bottom half 34' at one end of analytical device 30' as shown in FIG. 9. The member 226' and indentation 78' when engaged, provide a snap or latch fit engagement and generally cooperate to prevent the unintentional separation of cap 200' with device 30' when the cap 200' and the device 30' are attached. The cap 200' has slots 228' and 230' that engage with corresponding guide protrusions 68' and 70', respectively on the cap 200'. To further provide for a more secure fit between the cap 200' and the device 30', the guide arms 212' and 214' of the cap 200' may also have protrusions 238' and 240', respectively, that engage in a snap or latch fit manner with corresponding indentations 242' and 244' on device 30'. It will be readily apparent to those skilled in the art what other known means to provide for a releasable attachment of the cap 200 or 200' to any of the analytical devices of the present invention.

In the embodiments shown to have a cap as part of the analytical device, the analytical device may be fabricated to contain the membrane array of the present invention or alternatively, the two part membrane shown and described in Applicant's PCT IB/2003/005088 (the disclosure of which is incorporated herein by reference in its entirety). Briefly, the two part membrane comprises an upstream first separation membrane that contains a detection reagent and a downstream capture membrane containing a capture reagent.

Figure 10:
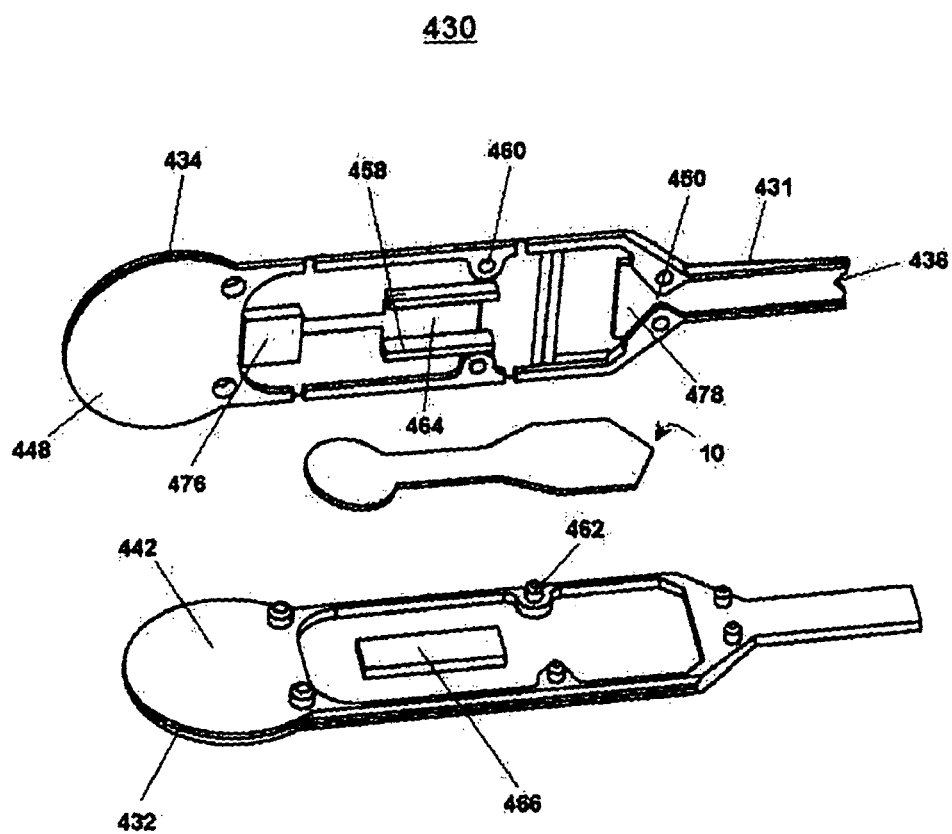
FIG. 10 is an exploded view of another embodiment featuring the membrane array of the invention in an analytical device configured for dipping into a reservoir of sample.

Another embodiment of an analytical device is shown in FIG. 10, in which the device is designed for dipping into a reservoir containing a fluid sample. In this embodiment the analytical device 430 is configured at one with an elongated portion 431 but functions in the same manner as the device of FIG. 2 or 3 except that the sample entry is provided by elongated portion 431 which can be dipped into the fluid sample, such as urine for example. The fluid sample enters into the analytical device 430 from the elongated sample flow channel formed from notch 436 in the upper half 434. The elongated sample flow channel terminates at the upstream end 18a of first separation membrane 18 of the membrane array 10. It will be noted that the downstream end of the sample flow channel is a constriction 450 so that sample flows uniformly into first separation membrane 18 at the apex 18a. There is also surface-to-surface contact between the first separation membrane edge 19 and the sidewalls of the widening area downstream of constriction 450 of upper half 434. It will be noted that the first separation membrane 18 is shaped and placed so that the sample enters through the first separation edge 19 of the first separation membrane 18 by capillary flow. To assist in holding the halves together, the bottom surface 448 of upper half 434 contain cylindrical indents 460 that are in register with cylindrical pillars 462 respectively, in the upper surface 442 of lower half 432. The membrane array 10 is held in position by resting on support structures 476 and 478 and is enclosed by rectangular protrusions 458 on the bottom surface 448 of the upper half 434 function and rectangular protrusion 466 on the top surface 442 of the lower half 432. There is also a viewing window 464 in the upper half 434 of analytical device 430 that is in registry with the analytical membrane 22 of the membrane array 10. In the embodiments shown to have elongated portion of the analytical device, the analytical device may be fabricated to contain the membrane array of the present invention or alternatively, the two part membrane shown and described in Applicant's PCT IB/2003/005088 (the disclosure of which is incorporated herein by reference in its entirety). Briefly, the two part membrane comprises an upstream first separation membrane containing a detection reagent and a downstream capture membrane containing a capture reagent.

It is within the scope of the present invention to detect an analyte or even multiple analytes in the fluid sample at one time. Accordingly, it will be appreciated by one skilled in the art that one or more detection reagents and/or one or more capture reagents can be deposited on the membrane array 10 of the present invention.

Any of a variety of labeled antibodies in the membrane array of the present invention available to the skilled artisan may be utilized. Metal and enzyme labels are commonly used. Metal labels are especially preferred due to their remarkable sensitivity. Amongst the metals, gold is most preferred principally because it is so widely employed for this type of reaction and its characteristics are so well understood. The preferred particle size for gold labeled antibodies employed in the invention is from about 20 to 65 nm, although appreciable variation can be tolerated depending on well understood factors such as the clinical cut off of the analyte and the affinity of the reactants. Additionally, a gold signal can be enhanced to become readily visible by the use of reducible silver salt which deposits as visible product. A typical reactive salt is silver lactate, which serves as the source of reducible silver ions, employing hydroquinone as a reducing agent. The metallic silver forms a readily discernible black deposit around each particle of gold.

Alternatively, if an enzyme label such as horseradish peroxidase is employed the reaction may be detected by the addition of hydrogen peroxide and a dye such as ortho phenylenediamine in accordance with standard procedures. Additional labels that may be used well within the scope of this invention are paramagnetic labels such as described in U.S. Pat. No. 6,046,585 (which is incorporated herein by reference in its entirety) which enable an even greater sensitivity for analyte detection.

The numerous analytes that may be detected in accordance with this invention are cardiac analytes associated with cardiovascular events such as myoglobin, troponins T (cTnT) and I (cTnI) and creatinine kinase MB (CK-MB). Furthermore, hormones associated with pregnancy or ovulation such as human chorionic gonadotropin (hCG) and luteinizing hormone (LH), respectively may also be detected using this invention or various embodiments thereof. It is also within the scope of this invention that other antigens for diseases such as cancer, specifically prostate cancer antigens (prostate serum antigen, PSA) may also be detected using this invention. Additional applications of this invention include the recognition of analytes associated with viral infections such as hepatitis, bacterial and fungal infection including *Helicobacter pylori* for gastrointestinal ulcers, other infections caused by *Bacillus anthracis, Pediculus humanis, Siphonaptera* and gram positive bacteria as *Streptococcus pyognes, Streptococcus pneumoniae* and *Streptococcus faecalis* are all non-limiting examples. This invention may also useful for detecting drugs including drugs of abuse. Enzymatic assays such as those that determine levels of glucose and in blood are also contemplated by the present invention. It will be recognized that the use of the devices is not limited to these specific analytes or, indeed, to whole blood but is equally applicable to other analytical procedures such as those mentioned above.

Although the invention will be described principally as applied to the so called sandwich assay, the skilled artisan will recognize that it is also applicable to other types of assays such as the competitive assay. In a competitive assay, an additional inclusion of a labeled antigen as the detection reagent in the first separation membrane 18 will compete with the analyte (antigen) in the sample for binding to the capture reagent such as for instance, an antigen binding molecule. In aspects of the invention, the antigen binding molecule may be a polyclonal or monoclonal antibody.

In an embodiment of the invention where the analyte is an antigen binding molecule such as an antibody the invention, the detection reagent may be a labeled antihuman IgG and the capture reagent is any a suitable immobilized antigen (or antigens) to the antibody (or antibodies) in the fluid sample. The numerous types of natural or synthetic antigens that may be employed and would be suitable for use with the present invention are well known to those of skill in the art. Examples of suitable antigens which can be immobilized include, but are not limited to, Human Immunodeficiency Virus (HIV) and hepatitis virus. Similarly, one skilled in the art would readily understand that in another embodiment of the invention, the detection reagent may also be a labeled antigen to an antibody in the fluid sample.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Without intending to be limiting in scope, the following example serves to illustrate various embodiments of the invention.

Example 1

A human cardiac troponin I test (TnI) device using one drop of whole blood sample is prepared according to current invention. For the analytical membrane, nitrocellulose (Whatman) with a pore size of about 5 μm was impregnated with both control and capture solutions using a conventional liquid dispenser. Control solution contains 1 mg/mL of goat anti-mouse IgG polyclonal antibodies (Arista Biologicals), and capture solution contains 2 mg/mL of an anti-troponin I monoclonal antibody (HyTest). Impregnated nitrocellulose was incubated at 37° C. for 30 minutes to immobilize the antibodies. The first separation membrane (Whatman) was sprayed with colloidal gold conjugate solution and then freeze dried to remove the water. The colloidal gold conjugate with a final OD of 2.2 at 540 nm was prepared from 40 nm gold particles (Arista Biologicals) and a monoclonal antibody specific to human cardiac troponin I (HyTest). An 8 μm nitrocellulose membrane (Whatman) was used as the second separation membrane. The membrane array is covered by a 25 μm transparent polyester tape (Adhesive Research) and supported by polystyrene backing tape (G & L Precision Die Cutting, Inc). The membrane array was assembled as shown in FIG. 1 and housed in an analytical device as shown in FIG. 2. The shape of the membrane array was obtained using a die-cutting tool. Testing of this analytical device using 35 μL of blood or serum demonstrated excellent plasma separation and sample flow in a testing procedure requiring approximately 10 minutes. The test achieved a sensitivity of 1 ng/mL of TnI.

Example 2

A human procalcitonin (PCT) test device using one drop of whole blood sample is prepared according to current invention. For the analytical membrane, nitrocellulose (Millipore) with a pore size of 5 μm was impregnated with both control and capture solutions using a conventional liquid dispenser. Control solution contains 1 mg/mL of goat anti-mouse IgG polyclonal antibodies (Arista Biologicals), and capture solution contains 2 mg/mL of anti-calcitonin sheep polyclonal antibodies (Brahms). Impregnated nitrocellulose was incubated at 37° C. for 30 minutes to immobilize antibodies. Detection membrane or plasma separator (Whatman) was sprayed with colloidal gold conjugate solution and then freeze dried to remove water. Gold conjugate, prepared from 40 nm gold particles (Arista Biologicals) and a monoclonal antibody specific to PCT (Brahms), had a final OD 1.5 at 540 nm. A 8 μm nitrocellulose membrane (Whatman) was used as the separation membrane. The test strip is covered by a 25 μm thick transparent polyester tape (Adhesive Research) and supported by polystyrene tape available from G & L Precision Die Cutting, Inc. Test strip was assembled as indicated in FIG. 1. The shape of the test strip was obtained using a die-cutting tool. Testing of this device using 35 μL of blood or serum demonstrated excellent plasma separation and sample flow. The testing procedure took approximately 25 min to complete. A sensitivity of 0.1 ng/mL of PCT was achieved.

Although preferred embodiments of the invention have been described herein in detail, it will be understood by those skilled in the art that variations may be made thereto without departing from the spirit of the invention or the scope of the appended claims.

The invention claimed is:

1. A membrane array for detecting one or more analytes in a fluid sample containing red blood cells, the membrane array comprising a separation membrane and an analytical membrane in fluid communication with one another, wherein:
   the separation membrane has a pore size of greater than a red blood cell to about 8 μm such that it retards red blood cells with negligible hemolysis and overlaps at least a portion of the analytical membrane; and
   the analytical membrane has a lower porosity than the separation membrane, wherein a small volume of about 10 μl to 50 μl of sample is used.

2. The membrane array of claim 1, wherein the analytical membrane comprises an upstream end and a downstream end, the upstream end being narrower than the downstream end.

3. The membrane array of claim 2, wherein the downstream end is circular.

4. The membrane array of claim 1, wherein the total dimensions of the membrane array are determined by the total absorption volume of the sample size.

5. The membrane array of claim 1, further comprising an upstream separation membrane, upstream of the separation membrane, the upstream separation membrane having a higher porosity than the separation membrane.

6. The membrane array of claim 5, wherein an upstream end of said upstream separation membrane forms an apex.

7. The membrane array of claim 5, wherein said membranes are fabricated from any type of porous membrane material that is blood compatible and body fluid compatible.

8. The membrane array of claim 7, wherein said material is selected from the group consisting of nitrocellulose, glass fiber membranes, synthetic fiber membranes, polyethersulfone membranes, pyrrolidone membranes, polyvinylidene difluoride membranes and combinations thereof.

9. The membrane array of claim 8, wherein said analytical membrane is fabricated from nitrocellulose or polyvinylidene difluoride.

10. The membrane array of claim 8, wherein said separation membrane is fabricated from nitrocellulose.

11. The membrane array of claim 5, wherein said upstream separation membrane has a pore size of about 8 µm to about 60 µm.

12. The membrane array of claim 1, wherein said separation membrane has a pore size is greater than about the size of a red blood cell up to about 8 µm.

13. The membrane array of claim 1, wherein said array is configured to receive a sample comprising body fluid.

14. The membrane array of claim 13, wherein said body fluid is whole blood.

15. The membrane array of claim 1, wherein said array is configured to receive a sample of about 10 µl to about 50 µl.

16. The membrane array of claim 1, wherein a backing card is provided as a support for said membrane array.

17. The membrane array of claim 1, wherein a transparent cover tape is provided over all or a part of said membrane array.

18. The membrane array of claim 17, wherein said transparent cover tape is a polyester film.

19. The membrane array of claim 1, comprising a detection reagent, wherein said detection reagent is a labeled antibody or antigen.

20. The membrane array of claim 1, comprising a capture reagent, wherein said capture reagent is an antibody or antigen.

21. The membrane array of claim 1, wherein said array comprises reagents to detect an analyte selected from the group consisting of calcitonin, myoglobin, troponin T (cTnT), troponin I (cTnI), creatinine kinase MB (CK-MB), human chorionic gonadotropin (hCG), luteinizing hormone (LH), cancer antigens, viral infection antigens, bacterial infection antigens, fungal infection antigens, drugs and combinations thereof.

22. The membrane array of claim 1, provided within an analytical device housing having a first and a second end.

23. The membrane array of claim 22, wherein one end of said analytical device is adapted to receive a removable cap, said cap facilitating the application of said sample using a sample transfer means to said membrane array.

24. The membrane array of claim 23, wherein the application of said sample is provided by a sample application means formed by an enclosure of upper and lower halves of said housing.

25. The membrane array of claim 22, wherein one end of said analytical device is adapted to be immersed in a sample such that the sample is provided to said membrane array through the immersed end of said analytical device.

26. An analytical device for detecting one or more analytes in a fluid sample containing red blood cells, the analytical device comprising a membrane array comprising a separation membrane and an analytical membrane in fluid communication with one another, wherein:
the separation membrane has a pore size of greater than a red blood cell and about 8 µm such that it retards red blood cells with negligible hemolysis and overlaps at least a portion of the analytical membrane; and
the analytical membrane has a lower porosity than the separation membrane, wherein a small volume of about 10 µl to 50 µl of sample is used.

27. The device of claim 26, wherein the analytical membrane comprises an upstream end and a downstream end, the upstream end being narrower than the downstream end.

28. The device of claim 27, wherein the downstream end is circular.

29. The device of claim 26, wherein the total dimensions of the membrane array are determined by the total absorption volume of the sample size.

30. The device of claim 26, further comprising an upstream separation membrane, upstream of the separation membrane, the upstream separation membrane having a higher porosity than the separation membrane.

31. The device array of claim 30, wherein an upstream end of said upstream separation membrane forms an apex.

32. The device of claim 30, wherein said membranes are fabricated from any type of porous membrane material that is blood compatible and body fluid compatible.

33. The device of claim 32, wherein said material is selected from the group consisting of nitrocellulose, glass fiber membranes, synthetic fiber membranes, polyethersulfone membranes, pyrrolidone membranes, polyvinylidene difluoride membranes and combinations thereof.

34. The device of claim 30, wherein said analytical membrane is fabricated from nitrocellulose or polyvinylidene difluoride.

35. The device of claim 30, wherein said separation membrane is fabricated from nitrocellulose.

36. The device of claim 30, wherein said upstream separation membrane has a pore size of about 8 µm to about 60 µm.

37. The device of claim 30, wherein said separation membrane has a pore size that is greater than about the size of a red blood cell up to about 8 µm.

38. The device of claim 26, wherein said array is configured to receive a sample comprising a body fluid.

39. The device of claim 38, wherein said body fluid is whole blood.

40. The device of claim 38, wherein said array is configured to receive a sample of about 10 µl to about 50 µl.

41. The device of claim 26, wherein a backing card is provided as a support for said membrane array.

42. The device of claim 26, wherein a transparent cover tape is provided over each, all or a part of said steps.

43. The device of claim 42, wherein said transparent cover tape is a polyester film.

44. The device of claim 26, comprising a detection reagent, wherein said detection reagent is a labeled antibody or antigen.

45. The device of claim 26, comprising a capture reagent, wherein said capture reagent is an antibody or antigen.

46. The device of claim 26, wherein said array comprises reagents to detect an analyte selected from the group consisting of calcitonin, myoglobin, troponin T (cTnT), troponin I (cTnI), creatinine kinase MB (CK-MB), human chorionic gonadotropin (hCG), luteinizing hormone (LH), cancer antigens, viral infection antigens, bacterial infection antigens, fungal infection antigens, drugs and combinations thereof.

* * * * *